United States Patent [19]
Earl

[11] Patent Number: 6,101,628
[45] Date of Patent: Aug. 15, 2000

[54] THUMB PROTECTION DEVICE

[75] Inventor: Tamela J. Earl, Marysville, Ohio

[73] Assignee: Honda of America Mfg., Inc., Marysville, Ohio

[21] Appl. No.: 09/267,961

[22] Filed: Mar. 12, 1999

[51] Int. Cl.[7] ............................... A41D 13/08; A61F 5/37
[52] U.S. Cl. ............................. 2/21; 2/16; 2/161.1; 2/167
[58] Field of Search ..................... 2/21, 16, 159, 2/20, 161.1, 162–164, 167, 907; 128/878, 879, 880–882; 602/1, 5, 6, 21, 22

[56] References Cited

U.S. PATENT DOCUMENTS

| | | |
|---|---|---|
| 4,374,439 | 2/1983 | Norman . |
| 4,383,336 | 5/1983 | Beckman et al. . |
| 4,651,350 | 3/1987 | Dawiedczyk . |
| 4,691,387 | 9/1987 | Lopez . |
| 4,779,289 | 10/1988 | Prouty . |
| 4,808,469 | 2/1989 | Hiles . |
| 4,850,341 | 7/1989 | Fabry et al. . |
| 5,031,640 | 7/1991 | Spitzer . |
| 5,050,596 | 9/1991 | Walasek et al. . |
| 5,121,962 | 6/1992 | Weber et al. . |
| 5,150,475 | 9/1992 | Hansen et al. . |
| 5,257,418 | 11/1993 | Jaskiewicz ..................................... 2/20 |
| 5,329,638 | 7/1994 | Hansen et al. . |
| 5,330,249 | 7/1994 | Weber et al. . |
| 5,581,809 | 12/1996 | Mah ............................................. 2/20 |
| 5,632,045 | 5/1997 | Chase et al. ............................. 2/161.6 |
| 5,640,712 | 6/1997 | Hansen et al. . |
| 5,653,643 | 8/1997 | Falone et al. . |
| 5,666,667 | 9/1997 | Hook, Jr. . |
| 5,829,061 | 11/1998 | Visgil et al. . |
| 5,933,868 | 8/1999 | Bender ..................................... 2/161.1 |

OTHER PUBLICATIONS

Website Publication, "the Dr. Spitzer® Glove for Carpal Tunnel Syndrome"; Shock Tek® Corporation, 4 pgs.; Jan. 18, 1999.

Primary Examiner—John J. Calvert
Assistant Examiner—Tejash Patel
Attorney, Agent, or Firm—Jenkens & Gilchrist

[57] ABSTRACT

The hand wrap according to the present invention dampens vibration and absorbs shock transmitted from a power tool to a thumb region of a hand. The hand wrap includes first and second elongated strips. The thumb ends of the strips are attached together and form a thumb pocket for receiving the thumb of the hand. The wrap ends of the strips wrap around a portion of the hand so as to secure the hand wrap to the hand with the aid of a releasable fastener located on one of the strips. A viscoelastic pad is disposed within the thumb pocket. A retaining layer is positioned over at least a portion of the viscoelastic pad and is attached to at least one of the strips for retaining the viscoelastic pad within the thumb pocket. The viscoelastic pad is preferably a continuous pad with a top region for positioning near the upper thumb knuckle and a bottom end for extending over a substantial portion of a thenar section of the palm.

42 Claims, 5 Drawing Sheets

THUMB PROTECTION DEVICE

FIELD OF THE INVENTION

The present invention relates generally to a thumb protective device and, in particular, to a hand wrap which includes a viscoelastic pad to dampen the vibration and absorb the shock that the thumb region of the hand typically encounters when grasping and operating a power tool.

BACKGROUND OF THE INVENTION

Some occupations, such as automotive assembly line personnel, require workers to grip various tools and machinery with their hands. Some of these tools and machinery transmit to the hand regular periodic energy known as vibrations in addition to bursts of high amplitude energy known as shocks. The transfer of shock to the hand may be, for example, due to the recoil experienced when a tool is activated while the transfer of vibration will typically occur during the standard operation of the tool. Common tools which require a constant hand grip and transmit vibration and shock to the hand include pneumatic guns (e.g. air guns), rivet guns, power saws, and power drills.

Prolonged use of such tools and the resulting transfer of vibrations and shocks can make such tools more difficult to use and may result in damage to the hand. This is especially true of both the front and back of the thumb and the thenar section of the palm (i.e. the mound section of the palm just below the base of the thumb) which often receives the brunt of this energy. While cushions and pads have been employed in some gloves to reduce the transmission of mechanical energy to the hand, particular attention has been directed to the palm of the hand and not so much to the thumb region. Dampening this energy in the thumb region can greatly enhance user comfort and performance.

However, as the padding and protection of a typical glove construction increases, the dexterity and sensitivity of the user generally decrease. For example, simple tasks, such as picking-up and setting down the air gun may consume more time and other tasks may even demand removal of the glove. For air gun users in particular, a glove can hinder the dexterity and sensitivity of the trigger finger making the air gun more dangerous to use. Also, some gloves tend to slip on the grasping surface of the tool, especially under conditions of vibration and shock. When slippage is encountered, the operator is required to further exert the hand muscles to secure the vibrating tool leading to further strain and fatigue of the hand.

Hence, a need exists for hand gear designed for vibration dampening and shock absorption to the entire thumb region while not significantly hindering the dexterity and sensitivity of the hand.

SUMMARY OF THE INVENTION

The hand wrap according to the present invention solves the aforementioned problems by dampening vibration and absorbing shock that is transmitted from a power tool to a thumb region of a hand. The hand wrap includes first and second elongated strips. The thumb ends the strips are attached together and form a thumb pocket for receiving the thumb. The wrap ends of the strips wrap around a portion of the hand so as to secure the hand wrap to the hand, preferably with the aid of a releasable fastener located on one of the strips.

A viscoelastic pad is disposed within the thumb pocket and against at least one of the strips. A retaining layer is positioned over at least a portion of the viscoelastic pad and is attached to at least one of the strips for retaining the viscoelastic pad within the thumb pocket. The viscoelastic pad is preferably a continuous pad with a top region that is positioned near the upper thumb knuckle and a bottom end for extending over a substantial portion of the thenar section of the palm.

The viscoelastic pad is preferably made of a gel-like viscoelastic material such as silicone gel. The pad absorbs the shock and dampens the vibrations of the operational tool by introducing a hysteresis into the periodic energy cycle. Because protection is focused in the thumb region where it is needed, the remaining four fingers are free to move about without being hindered by the wrap. In addition to the fingers being free, a portion of the palm is also free so as to provide the normal level of dexterity and sensitivity in those regions. While the beneficial features of the protective thumb device are described with reference to the hand wrap, the protective thumb device can also be used in gloves as well.

The invention will now be described in greater detail with reference to the accompanying drawings which illustrated exemplary embodiments of the invention.

Figure 1:
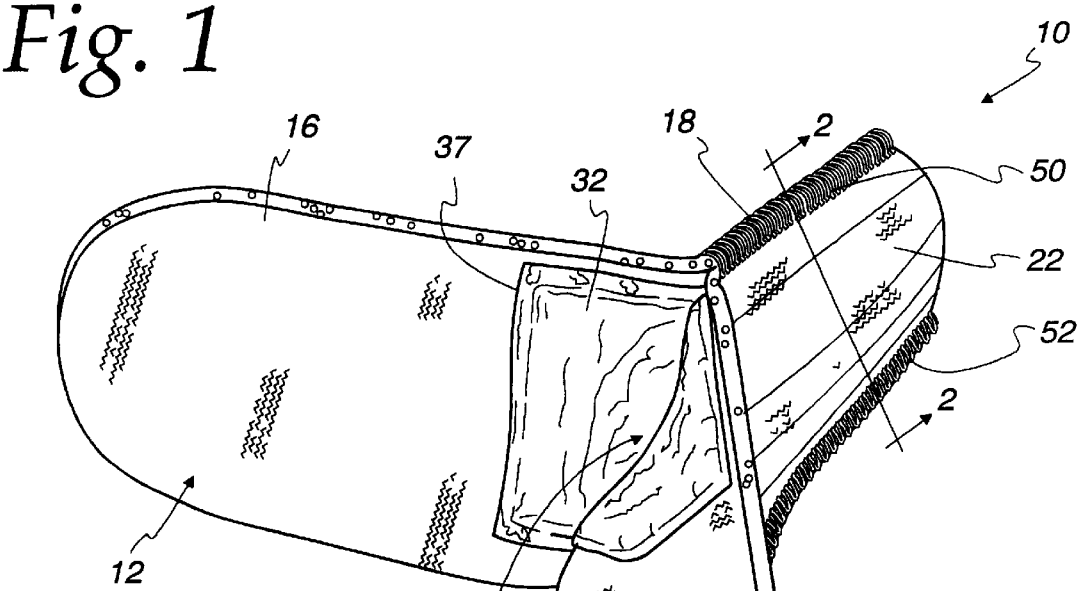
FIG. 1 is a perspective view of a hand wrap embodying the present invention.

While the invention is susceptible to various modifications and alternative forms, a specific embodiment thereof has been shown by way of example in the drawings and will herein be described in detail. It should be understood, however, that it is not intended to limit the invention to the particular forms disclosed. To the contrary, the intention is to cover all modifications, equivalents, and alternatives falling within the spirit and scope of the invention as defined by the appended claims.

DETAILED DESCRIPTION OF THE DRAWINGS

Figure 2:
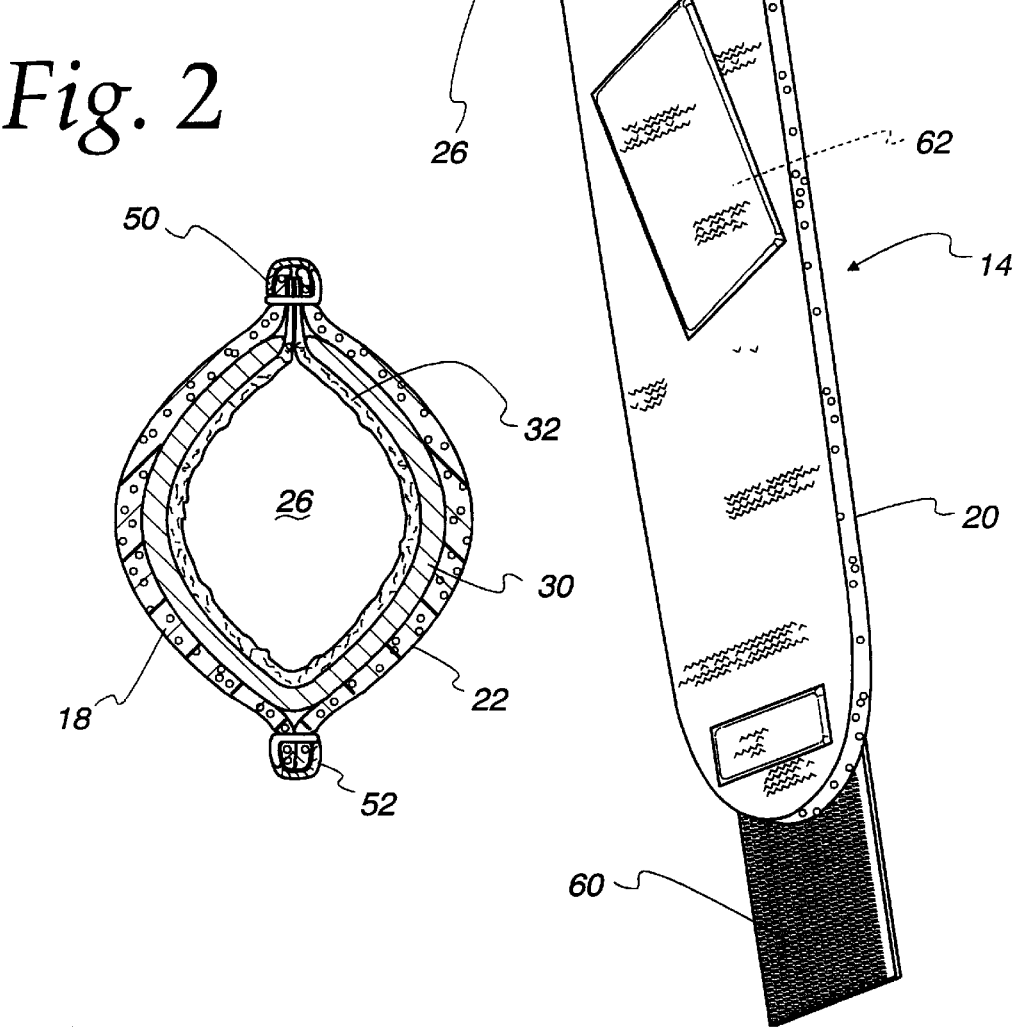
FIG. 2 is a cross-sectional view along line 2—2 of FIG. 1.
Figure 3:
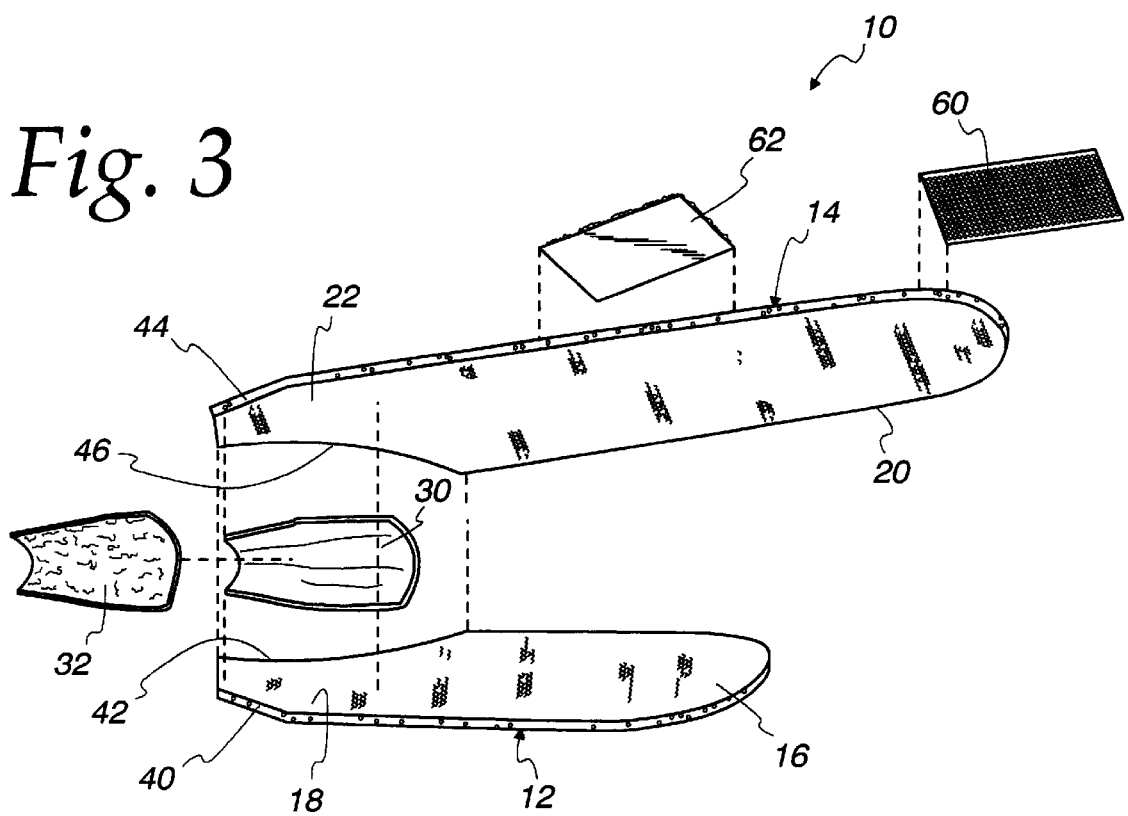
FIG. 3 is a exploded perspective view of the hand wrap of FIG. 1.

FIGS. 1–3 illustrate a hand wrap 10 embodying the present invention which includes a first elongated strip 12 and a second elongated strip 14. The first elongated strip 12 includes a first wrap end 16 and a first thumb end 18. Likewise, the second elongated strip 14 includes a second wrap end 20 and a second thumb end 22. The first and second thumb ends 18 and 22 define a thumb pocket 26 as shown best in FIG. 2.

Within the thumb pocket 26, the hand wrap 10 includes a viscoelastic pad 30 and a retaining layer 32. The viscoelastic pad 30 is preferably made of one continuous piece of material but may be made of several distinct pieces. The viscoelastic pad 30 is folded over such that it directly contacts the inner surface of both of the first and second thumb ends 18 and 22. Similarly, the retaining layer 32 is folded over and is in direct contact with the surface of the viscoelastic pad 30. The top portion of the viscoelastic pad 30 resides within the thumb pocket 26 while the bottom portion may reside at least partially outside the thumb pocket 26 as shown in FIG. 1.

The retaining layer 32 is preferably longer than the viscoelastic pad 30 such that the retaining layer 32 extends over the viscoelastic pad 30 and is attached to the first and second elongated strips 12 and 14 through an adhesive layer 37 which is located between the strips 12 and 14 and the retaining layer 32. Such an adhesive layer 37 may also be present at the uppermost region of the retaining layer 32 located deep within the thumb pocket 26. Alternatively, the retaining layer 32 may be sewn to the strips 12 and 14 at the position of the adhesive 37. Accordingly, the retaining layer 32 serves to maintain the position of the viscoelastic pad 30 within the thumb pocket 26.

As shown best in FIG. 3, the first thumb end 18 includes a first short edge 40 and a first long edge 42. Likewise, the second thumb end 22 includes a second short edge 44 and a second long edge 46. With the viscoelastic pad 30 and the retaining layer 32 between the first and second thumb ends 18 and 22, the short edges 40 and 44 are placed next to each other and the long edges 42 and 46 are placed next to each other. The pair of short edges 40 and 44 are sewn to each other at a short seam 50 while the pair of long edges 42 and 46 are likewise sewn together at a long seam 52. It is the shape of the short edges 40 and 44 and the long edges 42 and 46 which define the general shape of the thumb pocket 26. In a preferred embodiment, the thumb pocket 26 has a generally tubular shape, and more specifically, is slightly frustoconical. While the elongated strips 12 and 14 have been illustrated as two distinct pieces of material, they could also be made of a unitary piece of material.

Also, one or both of the loose ends of the retaining layer 32 may be placed between one of the pairs of edges 40, 44, or 42, 46 such that it is further attached to the strips 12 and 14 through one of the seams 50 or 52. As shown in FIG. 2, both loose ends of the retaining layer 32 are placed between the short edges 40 and 44 and sewn into the short seam 50.

To secure the hand wrap 10 to the hand of its user, at least one of the elongated strips 12 and 14 includes a fastening device for securing the hand wrap 10 on the hand. In one preferred embodiment, the second elongated strip 14 includes a hook device 60 and a closure device 62 having fibrous material. Such a hook device 60 and closure device 62 are commonly delivered in the form of a tape and are referred to as VELCRO® from Velcro USA, Inc. of Manchester, N.H. While the hook device 60 and closure device 62 is illustrated, other fastening devices may be employed such as a series of fastening snaps along one or both of the elongated strips 12 and 14.

Figure 4:
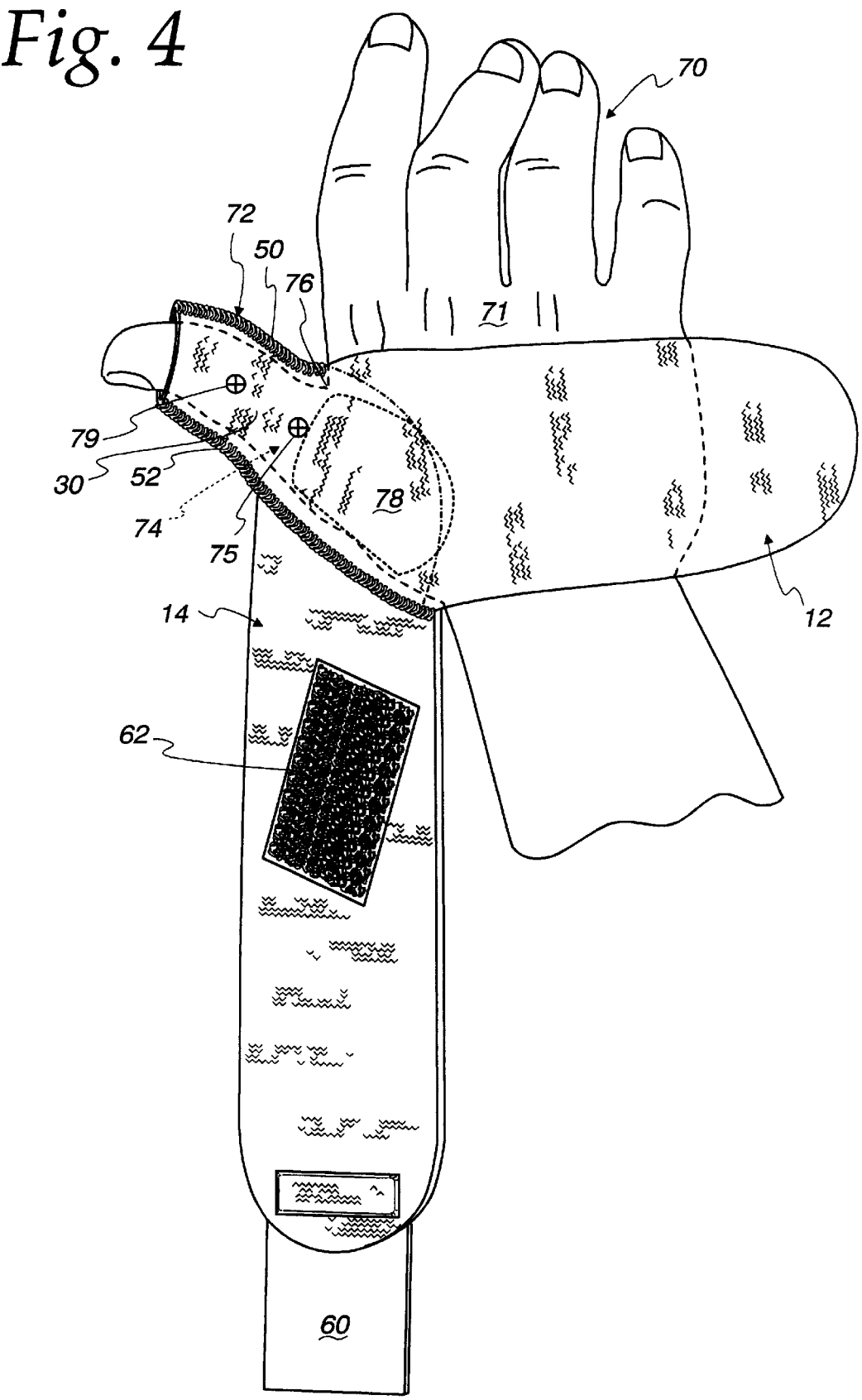
FIG. 4 is a perspective view of the hand wrap of FIG. 1 as it is being placed on the right hand.

FIG. 4 illustrates the first step by which a user would place the hand wrap 10 on his or her right hand 70. Since, the hand 70 is a right hand, a back 71 of the hand 70 is being viewed. The hand 70 includes a thumb 72 which would require protection from vibration or shock. The thumb 72 has a base region 74 which is located adjacent to the thumb metacarpophalangeal joint 75, the lower thumb joint adjacent to the thumb crotch 76. Below the thumb base 74 is the thenar section 78 of the palm, which is the mound section on the palm. Of course, the thenar section 78 is on the palm-side of the hand and would not be seen when viewing the back 71 of the hand 70. The user places the thumb pocket 26 over the thumb 72 such that the tip of the thumb 72 resides outside the hand wrap 10. The upper portion of the viscoelastic pad 30 is near the thumb interphalangeal joint 79, the upper thumb joint located directly below the thumb nail. Preferably, the viscoelastic pad 30 extends at least slightly above this upper thumb joint 79 toward the thumb tip so as to protect the upper thumb joint 79. And, the bottom portion of the viscoelastic pad 30 extends substantially into the thenar section 78. While the bottom portion is shown extending into only a section of the thenar section 78, the bottom portion of the pad 30 can be configured to cover the entire thenar section 78.

The short seam 50 extends along the inner portion of the thumb 72 and terminates adjacent to the thumb crotch 76. Accordingly, the short seam 50 has a length in the range from approximately 1.25 inches to 1.75 inches. The long seam 52 extends along the periphery of the thumb 72 and the portion of the palm adjacent to the thenar section 78. To accomplish this, the long seam 52 has a length of at least about 2 inches.

The first elongated strip 12 extends across the back 71 and has a sufficient length to extend into at least a portion of the palm of the hand 70. The second elongated strip 14 has a sufficient length to extend around the palm of the hand 70, extend over the free end of the first elongated strip 12, and wrap around the back 71 of the hand 70. The hook device 60 is then attached to the closure device 62. To provide the proper fastening of the hand wrap 10, the distance between the hook device 60 and the closure device 62 is approximately equal to the distance needed to circumscribe the entire hand. It should be noted that the hand wrap 10 may also include padding to protect the back 71 of the hand 70. For example, the first elongated strip 12 may include a second viscoelastic pad as well.

While the hand wrap 10 has been described with respect to the right hand, it also can be used on the left hand. If the hand 70 of FIG. 4 is viewed as a left hand such that the back 71 is the palm, it can be readily visualized how the hand wrap 10 is placed on the left hand. Instead of the first elongated strip 12 being placed across the back 71, it is placed across the palm. The second elongated strip 14 is then wrapped around the back of the left hand and over the first elongated strip 12 in the palm of the left hand.

The thumb pocket 26 is shown to include the viscoelastic pad 30 throughout its inner circumference thereby giving the viscoelastic pad 30 a generally tubular shape or, more specifically, a slightly frustoconical shape. Because the viscoelastic pad 30 is present within the entire thumb pocket 26, it is useful on either hand. However, the viscoelastic pad 30 can be placed primarily on just one of the first and second elongated strips 12 and 14 at their respective thumb ends 18 and 22 if it is to be used on one hand only. Selecting which of the two strips 12 and 14 against which to place the viscoelastic pad 30 is dictated by the preferred hand for wrapping (i.e. either the right hand or the left hand). In other words, the viscoelastic pad 30 would be placed against the strip 12 or 14 which would be the primary surface for engaging the hand tool.

Figure 5:
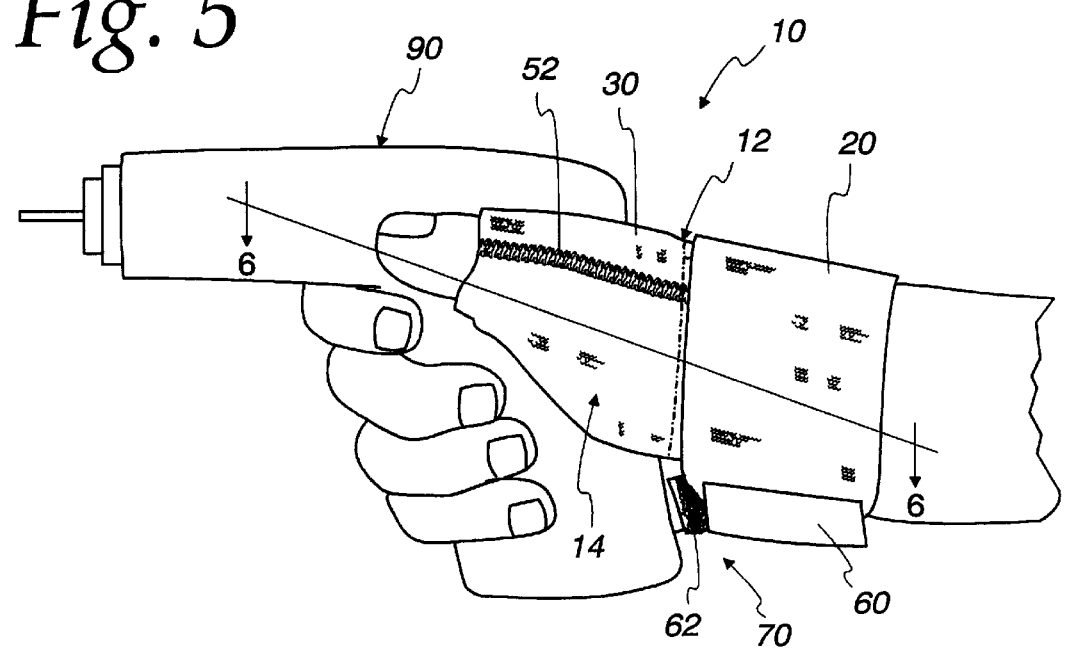
FIG. 5 is a side view of the hand wrap in use as the hand grasps a power tool.
Figure 6:
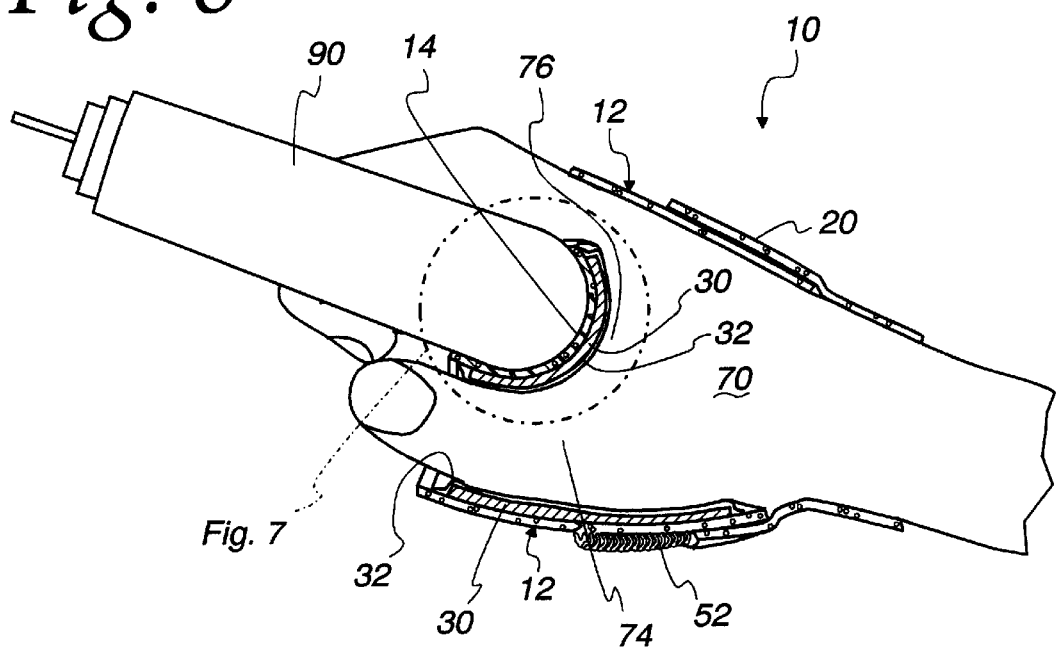
FIG. 6 is a cross-sectional view along line 6—6 of FIG. 5.
Figure 7:
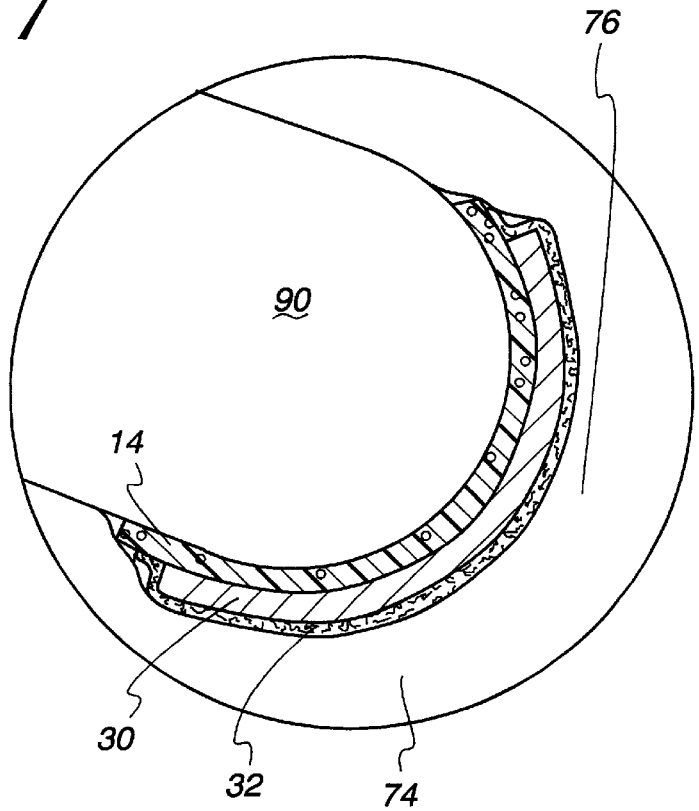
FIG. 7 is an expanded view of FIG. 6 with additional detail provided at the interface between the hand and the power tool.

FIGS. 5–7 illustrate the hand wrap 10 being used with an air gun 90. The air gun 90 is being held by the hand 70 of the operator who has fully installed the hand wrap 10 on the right hand 70. As shown best in FIG. 5, the dividing line between the first and second elongated strips 12 and 14 is along the long seam 52. Once the second wrap end 20 of the second elongated strip 14 has been passed through the palm and wrapped around the back of the hand, the hook device 60 is then placed against the closure device 62 at the underside of the palm near the wrist.

FIG. 6, which is a cross-section along line 6—6 of FIG. 5, and FIG. 7 illustrate in detail the interaction between the hand 70 and the air gun 90. The air gun 90 has an arcuately shaped back portion which is in direct contact with the second elongated strip 14. The viscoelastic pad 30 is sandwiched between the second elongated strip 14 and the retaining layer 32 which directly contacts the hand 70. Accordingly, any vibration which is transmitted from the air gun 90 is dampened by the viscoelastic pad 30 before encountering the hand 70. Likewise, the viscoelastic pad 30 also absorbs shock produced by the air gun 90.

In a preferred embodiment, the first and second elongated strips 12 and 14 are made of a stretchable material such as Neoprene with a thickness of about 0.1 inch. Because the retaining layer 32 is the material contacting the skin, the retaining layer 32 is preferably made of a cotton fleece material having a soft texture that provides comfort to the user of the hand wrap 10. The viscoelastic pad 30 is preferably made of a gel-like viscoelastic material such as silicone gel. The viscoelastic pad 30 has a thickness in the range from about 0.05 inch to about 0.25 inch so as to provide the necessary protection without compromising dexterity and sensitivity. In addition, the invention contemplates the use of other gel-like viscoelastic materials such as vinyl plastisols and also polyurethane elastomers. In one preferred embodiment, the hand wrap 10 employs a viscoelastic pad 30 made of silicone gel having a thickness of about 0.1 inch and has successfully reduced the stress to the thumb region of the hand for users of a typical air gun. Further, because the hand wrap 10 leaves the four fingers and a portion of the palm free from obstruction, the sensitivity and dexterity of the hand 70 is only slightly compromised by adding the thumb protective device.

Figure 8:
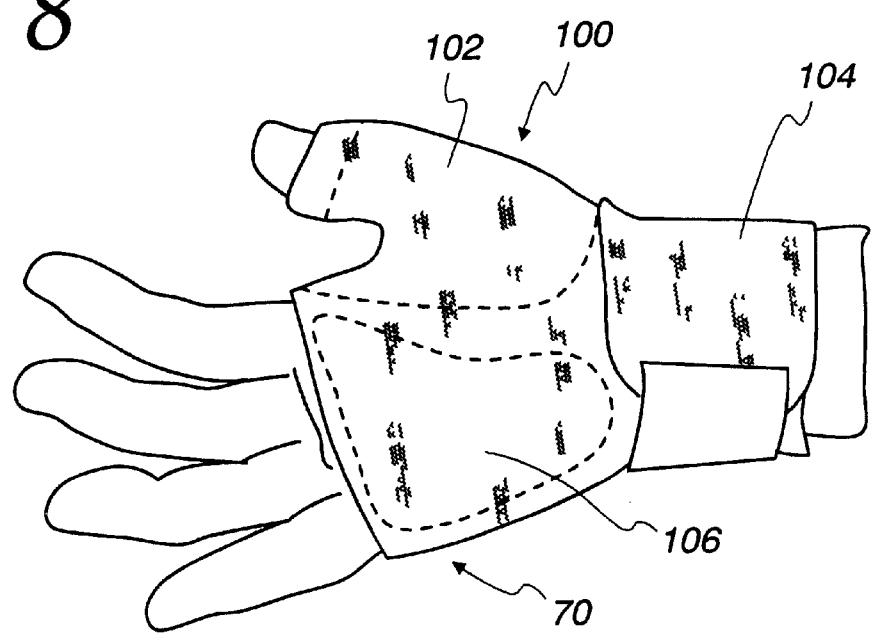
FIG. 8 is a side view of the thumb protective device as applied to a work glove lacking finger and thumb sections.

FIG. 8 illustrates an alternative embodiment employing the thumb protection device in the form of fingerless glove 100. The fingerless glove 100 includes a viscoelastic material 102 in the thumb region providing for the same type of protection as the viscoelastic pad 30 described with reference to FIGS. 1–7. The viscoelastic material 102 is held in place in the fingerless glove 100 in the same manner as described above with reference to FIGS. 1–7. In use, the user of the fingerless glove 100 inserts his or her hand 70 into the glove and secures the glove on the hand with the securing strip 104 adjacent to the wrist. The fingerless glove 100 may also include a palm pad 106 which assists in dampening vibration and absorbing shock in portions of the palm outside the thenar region. While the palm pad 106 can also be made of a viscoelastic material, it can also be made of other types of padding. Further, the viscoelastic pad 102 can be made larger so that it effectively covers the palm portion of the hand so as to eliminate the need for the palm pad 106.

Figure 9:
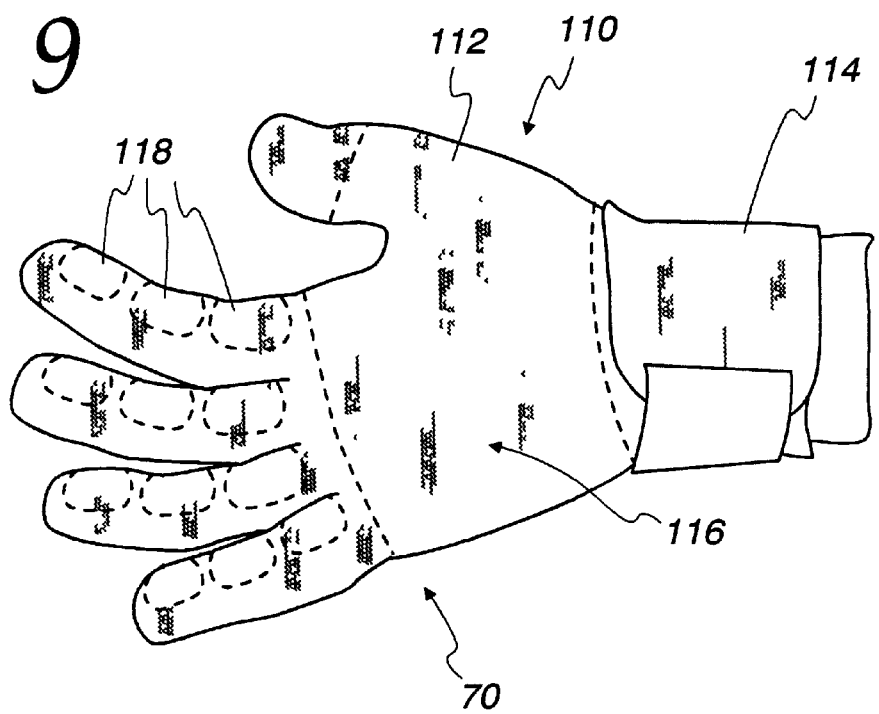
FIG. 9 is a side view of the thumb protective device as applied to a typical work glove.

FIG. 9 illustrates yet another alternative embodiment of the thumb protection device as applied to a traditional glove 110. Here, the glove 110 includes a viscoelastic pad 112 which extends entirely through a palm portion 1 16 of the hand and wraps around the back of the hand. The viscoelastic pad 112 is held inside the glove in the same manner as described with reference to FIGS. 1–7 and serves the same purpose as the viscoelastic pad 30 of FIGS. 1–7. The glove 110 is secured on the hand in one of many ways including, for example, a securing strip 114 placed adjacent to the wrist of the hand 70. Further, the traditional glove 110 may also include finger padding 118 in the regions of the four fingers. This finger padding 118 may be discrete padding on each finger placed between the joints as shown in FIG. 9 or may be one elongated pad extending along a substantial portion of the length of the finger. The finger padding 118 can also be made of a viscoelastic material. While FIG. 9 illustrates one continuous pad 112 extending around the hand 70, it can be made similar to FIG. 8 and have discrete pads for the thumb region and for the palm region. Or, the glove 110 can simply have a viscoelastic pad to protect the thumb region of the hand.

While the present invention has been described with reference to one or more preferred embodiments, those skilled in the art will recognize that many changes may be made thereto without departing from the spirit and scope of the present invention which is set forth in the following claims.

What is claimed is:

1. A hand wrap for dampening vibration and absorbing shock transmitted from a power tool to a thumb region of a hand, comprising:

a first elongated strip having a first thumb end and a first wrap end for passing across a portion of said hand;

a second elongated strip having a second wrap end for passing across said first wrap end of said first elongated strip and wrapping around said hand, said second elongated strip including a second thumb end attached to said first thumb end, said first and second thumb ends defining a thumb pocket for receiving a thumb of said hand;

a viscoelastic pad disposed within said thumb pocket and against at least one of said first and second thumb ends of said strips;

a retaining layer positioned over at least a portion of said viscoelastic pad, said retaining layer being attached to at least one of said first and second thumb ends for retaining said viscoelastic pad within said thumb pocket; and a releasable fastener for securing said second wrap end of said second elongated strip around said hand.

2. The hand wrap of claim 1, wherein said thumb pocket has a frustoconical shape.

3. The hand wrap of claim 1, wherein said releasable fastener includes a hook and loop closure, said hook and loop closure being located on said second strip.

4. The hand wrap of claim 3, wherein said hook and loop closure includes a piece of hook tape attached to one surface of second elongated strip and a piece of fibrous material attached to an opposing surface said second elongated strip.

5. The hand wrap of claim 1, wherein said first and second strip are made from a stretchable elastic material.

6. The hand wrap of claim 1, wherein said viscoelastic pad is made of a silicone gel.

7. The hand wrap of claim 1, wherein said retaining layer is larger than said viscoelastic pad and, with said at least one of said first and second thumb ends, encloses said viscoelastic pad.

8. The hand wrap of claim 7, further including an adhesive layer between said retaining layer and said at least one of said first and second thumb ends, said adhesive layer providing said attachment of said retaining layer to said at least one of said first and second thumb ends.

9. The hand wrap of claim 8, wherein said retaining layer is made from a fleece material.

10. The hand wrap of claim 1, wherein said thumb pocket includes an open end for exposing a tip of said thumb and said viscoelastic pad includes a top region for extending above an upper thumb knuckle.

11. The hand wrap of claim 1, wherein said second elongated strip has a length to encompass said hand at least once.

12. The hand wrap of claim 1, wherein said viscoelastic pad has a top region and a bottom region, said top region being disposed within said thumb pocket and said bottom region being at least partially disposed outside of said thumb pocket.

13. The hand wrap of claim 12, wherein said bottom region of said viscoelastic pad has a length to extend beyond a base of said thumb and cover a substantial portion of a thenar region of said palm.

14. The hand wrap of claim 1, wherein said viscoelastic pad is generally tubular shaped and positioned against both of said first and second thumb portions for providing protection substantially entirely around said thumb pocket.

15. The hand wrap of claim 14, wherein said viscoelastic pad has a top region and a bottom region, said top region being disposed within said thumb pocket and said bottom region being at least partially disposed outside of said thumb pocket, said bottom region of said viscoelastic pad has a length to extend beyond said thumb base and cover a substantial portion of a thenar region of said palm.

16. The hand wrap of claim 1, wherein said first and second strips are two distinct pieces of material.

17. The hand wrap of claim 16, wherein said first and second elongated strips are attached at a short seam and a long seam.

18. The hand wrap of claim 17, wherein said short seam has a length of approximately 1.25 inches to 1.75 inches so as to extend from the thumb crotch to a point near the upper thumb knuckle.

19. The hand wrap of claim 17, wherein said long seam has a length of at least about 2.0 inches so as to extend from a point near the upper thumb knuckle to a point adjacent to the thenar section of said thumb.

20. A thumb protection device for protecting a thumb of a hand from mechanical energy, comprising:
   a pocket defined by a layer of material having an inner section for confronting a palm-side of said thumb and an outer section for confronting a nail-side of said thumb, said layer of material being a portion of a hand wrap; and
   a continuous viscoelastic pad positioned within said pocket and against said inner section of said layer of material, said viscoelastic pad having a top region for positioning near an upper thumb knuckle and a bottom region for extending over a substantial portion of a thenar section of said palm.

21. The thumb protection device of claim 20, wherein said layer of material is two distinct pieces of material.

22. The thumb protection device of claim 20, wherein said thumb pocket is generally tubular and said viscoelastic pad is also generally tubular so as to extend along an inner circumference of said thumb pocket.

23. The thumb protection device of claim 22, wherein said viscoelastic pad is a continuous sheet having two ends, said sheet being folded over so that said two ends are adjacent to each other thereby producing said generally tubular shape.

24. The thumb protection device of claim 20, further including means for retaining said viscoelastic pad within said pocket.

25. The thumb protection device of claim 24, wherein said retaining means includes a cloth layer placed over said viscoelastic pad.

26. The thumb protection device of claim 25, wherein said cloth layer entirely covers said viscoelastic pad.

27. The thumb protection device of claim 26, wherein retaining means further includes an adhesive layer placed between said cloth layer and said inner section of said layer of material.

28. The thumb protection device of claim 20, wherein said top region extends at least slightly above said upper thumb knuckle.

29. A thumb protection device for protecting a thumb from mechanical energy, said thumb protection device capable of fitting onto and protecting a thumb on a right hand and a left hand, said thumb protecting device comprising:
   a first strip having a first wrap end;
   a second strip having a second wrap end, said second elongated strip being attached to and being longer than said first elongated strip;
   a thumb pocket for receiving said thumb and being defined by said first and second elongated strips;
   a viscoelastic pad disposed within said thumb pocket;
   a releasable fastener for securing said second wrap end of said second elongated strip around said hand; and
   wherein a first configuration said thumb of one of said right and left hands is placed into said thumb pocket, said first wrap end is placed across the palm of said one hand, and said second wrap end extends across the back of said one hand and wraps across the palm of said one hand over said first wrap end; and
   wherein a second configuration said thumb of the other of said right and left hands is placed into said thumb pocket, said first wrap end is placed across the back of said other hand, and said second wrap end extends across the palm of said other hand and wraps across the back of said other hand over said first wrap end.

30. The thumb protection device of claim 29, wherein said first and second strips are two distinct pieces of material.

31. The thumb protection device of claim 29, wherein said viscoelastic pad has a generally tubular shape so as to extend substantially entirely throughout said thumb pocket.

32. The thumb protection device of claim 31, wherein said viscoelastic pad is a continuous sheet having two ends, said sheet being folded over so that said two ends are adjacent to each other thereby producing said generally tubular shape.

33. The thumb protection device of claim 29, further including means for retaining said viscoelastic pad with said pocket.

34. The thumb protection device of claim 33, wherein said retaining means is a cloth layer that covers said viscoelastic pad, said cloth layer being attached to at least one of said first and second strips.

35. The thumb protection device of claim 29, wherein said viscoelastic pad is of a length sufficient to extend over a substantial portion of a thenar region of said palm.

36. The thumb protection device of claim 29, wherein said viscoelastic pad has a top portion for extending above an upper thumb knuckle and a bottom portion for extending over a substantial portion of said thenar region, at least a section of said bottom portion being outside of said thumb pocket.

37. A method of operating a power tool while reducing the mechanical energy transmitted from said power tool to a thumb region of a hand, comprising the steps of:
   providing a thumb protection device defining a thumb pocket with a viscoelastic pad placed therein, said thumb protection device being part of a hand wrap;

inserting a thumb into said thumb pocket, said viscoelastic pad extending from a point near an upper thumb knuckle to a thenar section of said palm;

wrapping pieces of said hand wrap around said hand to secure said thumb protection device on said thumb;

grasping said power tool such that said viscoelastic pad is positioned between said power tool and said thumb region; and actuating said power tool.

38. The method of claim 37 wherein said point near said upper thumb knuckle is at least slightly above said upper thumb knuckle.

39. The method of claim 37 wherein said thumb pocket has an open top portion and said step of inserting said thumb into said thumb pocket includes exposing a tip of said thumb through said open top portion.

40. The method of claim 37 wherein said viscoelastic pad covers a substantial portion of said thenar section of said palm.

41. The method of claim 37 wherein said viscoelastic pad is made of a silicone gel.

42. The method of claim 37 wherein said thumb protection device further includes a layer of material for retaining said viscoelastic pad within said thumb pocket, and said step of inserting said thumb into said thumb pocket includes contacting said retaining layer with said thumb.

* * * * *